United States Patent
Nevare et al.

(10) Patent No.: US 10,266,478 B2
(45) Date of Patent: Apr. 23, 2019

(54) PROCESS FOR THE PREPARATION OF HYDROXYL FUNCTIONAL ESTERS AND POLYESTERS THEREFROM

(71) Applicant: Council of Scientific and Industrial Research, New Delhi (IN)

(72) Inventors: Yogesh Ramesh Nevare, Maharashtra (IN); Susheela Bhaskar Idage, Maharashtra (IN); Bhaskar Bhairavnath Idage, Maharashtra (IN); Swaminathan Sivaram, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/547,382

(22) PCT Filed: Jan. 29, 2016

(86) PCT No.: PCT/IN2016/050033
§ 371 (c)(1),
(2) Date: Jul. 28, 2017

(87) PCT Pub. No.: WO2016/120893
PCT Pub. Date: Aug. 4, 2016

(65) Prior Publication Data
US 2018/0022681 A1 Jan. 25, 2018

(30) Foreign Application Priority Data
Jan. 29, 2015 (IN) .............................. 256/DEL/2015

(51) Int. Cl.
| C07C 69/68 | (2006.01) |
| C07C 67/08 | (2006.01) |
| C08G 63/06 | (2006.01) |
| C08G 63/78 | (2006.01) |
| C08G 63/82 | (2006.01) |
| C08G 63/85 | (2006.01) |

(52) U.S. Cl.
CPC .............. C07C 67/08 (2013.01); C07C 69/68 (2013.01); C08G 63/06 (2013.01); C08G 63/78 (2013.01); C08G 63/823 (2013.01); C08G 63/85 (2013.01)

(58) Field of Classification Search
CPC ............................... C07C 69/68; C08G 63/823
See application file for complete search history.

(56) References Cited

U.S. PATENT DOCUMENTS

| 2,371,281 A | 3/1945 | Claborn | |
| 2005/0215453 A1* | 9/2005 | Teissier | C11D 7/5022 510/421 |
| 2009/0200511 A1* | 8/2009 | Allen | A61K 8/37 252/182.12 |

FOREIGN PATENT DOCUMENTS

| CA | 2656697 | 1/2008 |
| EP | 1666968 | 6/2006 |
| WO | WO-1999043669 | 9/1999 |
| WO | WO-2016120893 | 8/2016 |

OTHER PUBLICATIONS

Ajioka, Masanobu, et al., "Basic Properties of Polylactic Acid Produced by The Direct Condensation Polymerization of Lactic Acid", *Bulletin of the Chemical Society of Japan*, 68(8), (1995), 2125-2131.

Grala, Agnieszka, et al., "Chemoselective alcoholysis of lactide mediated by a magnesium catalyst: an efficient route to alkyl lactyllactate", *Dalton Trans.*, 40, (2011), 4042-4044.

Marques, Dina S., et al., "Bulk Polytransesterification of L-Lactic Acid Esters: An Alternative Route to Synthesize Poly(lactic acid)", *Journal of Applied Polymer Science*, vol. 125, Issue S2, (2012) E283-E289.

Moon, Sung Il, et al., "Melt Polycondensation of L-Lactic Acid with Sn(II) Catalysts Activated by Various Proton Acids: A Direct Manufacturing Route to High Molecular Weight Poly(L-lactic acid)", *J. Polym. Sci. A Polym. Chem.*, 38: 1673-1679, (2000), 1673-1679.

Phomphrai, Khamphee, et al., "Facile alcoholysis of L-lactide catalysed by Group 1 and 2 metal complexes", *Dalton Trans.*, No. 23. (2008), 3048-3050.

Shyamroy, Subarna, et al., "High molecular weight poly(L-lactic acid)s by polyesterification using diisopropylcarbodiimide (DIPC) and 4-(dimethylamino) pyridinium-p-toluene sulfonate (DPTS)", *Polymer Bulletin*, vol. 72(3), (Mar. 2015), 405-415.

"International Application No. PCT/IN2016/050033, International Search Report and Written Opinion dated Oct. 4, 2016", (Oct. 4, 2016), 14 pgs.

* cited by examiner

*Primary Examiner* — Gregory Listvoyb
(74) *Attorney, Agent, or Firm* — Schwegman Lundberg & Woessner, P.A.

(57) ABSTRACT

The present invention relates to a novel process for the preparation of a linear monomer alkyl lactyl lactate by a simple esterification reaction of acid with ester in presence of suitable catalysts or reagents. The present invention further relates to a process for the preparation of poly acid from alkyl lactyl lactate by using suitable catalyst.

6 Claims, 2 Drawing Sheets

PROCESS FOR THE PREPARATION OF HYDROXYL FUNCTIONAL ESTERS AND POLYESTERS THEREFROM

PRIORITY CLAIM TO RELATED APPLICATIONS

This application is a U.S. national stage application filed under 35 U.S.C. § 371 from International Application Serial No. PCT/IN2016/050033, which was filed 29 Jan. 2016, and published as WO2016/120893 on 4 Aug. 2016, and which claims priority to India Application No. 256/DEL/2015, filed 29 Jan. 2015, which applications and publication are incorporated by reference as if reproduced herein and made a part hereof in their entirety, and the benefit of priority of each of which is claimed herein.

FIELD OF THE INVENTION

The present invention relates to a process for the preparation of hydroxyl functional esters. More particularly the present invention relates to a novel process for the preparation of a monomer, namely alkyl lactyl lactate, by a simple esterification reaction of acid with an ester. The present invention further relates to a process for the preparation of polymers from alkyl lactyl lactate in presence of a suitable catalyst.

BACKGROUND AND PRIOR ART

Poly (lactic acid) (PLA) is biodegradable and biocompatible aliphatic polyester which has useful properties and is derived from renewable feedstocks. Poly (lactic acid) has been reported to have useful applications and is a replacement for petroleum derived polymers such as polyolefins, polyesters and polystyrene (Auras, R.; Lim, L-T; Selke, S. E. M.; Tsuji, H. eds., Poly (Lactic acid): Synthesis, structures, properties, processing and applications; Wiley: N.J., USA., 2010).

PLA is generally prepared by three methods. One, by the Ring Opening Polymerization (ROP) of a cyclic lactide, derived from the dimerization of lactic acid. ROP is the preferred method because it results in high yields of the polymer with high molecular weights. However, ROP requires the preparation of the cyclic dimer of the lactic acid in a separate step followed by purification by melt crystallization. These steps add to the complexity as well as to the cost of producing PLA by ROP. The second method is by the dehydration-polycondensation of aqueous lactic acid. Lactic acid is normally obtained as 80-90% aqueous solution from a fermentor. Direct polycondensation of the aqueous solution requires first removal of water by using an organic solvent as an entrainer for azeotropic distillation followed by polycondensation of the dehydrated lactic acid (water content less than 3 ppm) in presence of a catalyst (Ajioka, M.; Enomoto, K.; Suzuki, K.; Yamaguchi, A.; Bulletin of Chemical Society Japan, 68, 2125-2131, 1995; Moon, S-L.; Lee, C. W.; Miyamoto, M.; Kimura, Y.; Journal of Polymer Science, Polymer Chemistry, 38, 1673-1679, 2000). This process is characterized by very slow rates of polymerization, formation of cyclic oligomers along with the linear polymer, poor color of the final product and difficulties in attaining adequate molecular weights. The third method is by the polyesterification of linear oligomers of PLA of low molecular weight using an esterification catalyst under anhydrous conditions. Though this method yields polymers with reasonable molecular weights, it suffers from the disadvantage that the esterification catalyst is needed in stoichiometric quantities (Shyamroy, S.; Garnaik, B.; Sivaram, S.; Polymer Bulletin, 72(3), 12-, 2014).

Consequently, the latter two methods for producing PLA are not used in commercial practice.

The difficulties in polymerizing aqueous lactic acid arise out of many factors. Lactic acid molecule has two functional groups, i.e. a hydroxyl and a carboxylic acid group which can undergo both intermolecular and intramolecular esterification reactions which are catalyzed by the acid itself. The first step is intermolecular esterification of one unit of lactic acid with a second unit of another lactic acid to form a dimer called lactoyl lactic acid. Further condensation of lactoyl lactic acid proceeds with the removal of water to higher oligomers. The formation of cyclic dimer, lactide, also occurs during this reaction by intramolecular esterification of lactoyl lactic acid or by breakdown of higher oligomers. Both these reactions are equilibrium controlled reactions and proceed with the removal of water. Removal of water is difficult as the polymer molecular weight increases. This causes the equilibrium to reverse, leading to low molecular weight polymers along with substantial amount of cyclic oligomers.

One method to obviate this problem is to provide conditions of polymerization where, instead of water, one can remove more volatile alcohols. In fact such an approach is the basis for the large volume manufacture of aromatic polyesters from aromatic diesters and aliphatic diols, e.g., polyethylene terephthalate which is accompanied by the removal of methanol. Alkyl lactates could also undergo such a reaction. It is interesting to note that during the purification of lactic acid from the fermentation process methyl lactate is an intermediate. Thus, they are available readily.

However, alkyl lactates cannot be polymerized, because they possess low boiling points and they distill before the actual temperature needed for polymerization is reached. Therefore, such reactions are accompanied by poor yields (Marques, D. S; Gil, M. H.; Cristina, M. S.; Baptista, M. S. G.; Journal of Applied Polymer Science, 125(S2), E283-E289, 2012).

Another method to obviate the drawbacks of the aforementioned processes is to provide a self polymerizable monomer containing a hydroxyl group and an alkyl ester group, whose boiling point is substantially higher than the temperatures normally employed for polycondensation. Furthermore, such a monomer must be capable of being synthesized in high chemical purity and be obtained in anhydrous conditions.

One such monomer is an alkyl ester of lactoyl lactic acid, namely, alkyl lactylactate. U.S. Pat. No. 2,371,281 discloses the process for the synthesis of alkyl lactoyl lactate comprising the steps of alcoholysis of lactide in benzene using sulfuric acid as catalyst at 70-75° C. The resulting alkyl lactyl lactate had high boiling points and could be purified by vacuum distillation. Canadian Pat. No. 2656697 discloses a process for making an alkyl lactyl lactate by the reaction of cyclic lactide with a hydroxyl containing compound in presence of acid catalyst in the temperature range of 20° C. to 70° C. Other catalysts have also been reported for the alcoholysis of cyclic lactides to produce alkyl lactyl lactate. For example a magnesium catalyst was reported to yield high yields of ethyl and methyl lactyl lactates (Grala, A.; Ejfler, J.; Jerzykiewicz, L. B.; Sobota, P.; Dalton Transactions, 40, pp 4042-4044, 2011). Metal amides have been used as catalysts for the reaction of methanol with cyclic lactide to yield methyl lactyl lactate (Phomphrai, K.; Pracha, S.; Phonjantheuk, P; Pohmakotr, M.; Dalton Transactions, pp 3048-3050, 2008).

However all the above methods suffer from the disadvantage that the preparation of an alkyl lactyl lactate requires the cyclic lactide as the starting material. The cyclic lactide in high purity has to be made from oligomers of lactic acid followed by melt purification involving multiple steps.

Therefore, one of the objectives of the present invention is to prepare alkyl esters of lactyl lactic acid from a simple esterification of lactic acid with alkyl lactate. Another objective of the present invention is to examine the possibility of transesterification—polycondensation of alkyl lactyl lactate to poly lactic acid. Alkyl lactyl lactates are expected to have high boiling points, low vapour pressures, can be easily purified by distillation, are hydrophobic and possess no acid functionality.

Consequently, one of the objectives of this invention is to explore an efficient method for the synthesis of an alkyl lactyl lactate by the direct esterification reaction of a alkyl ester of lactic acid with lactic acid using a suitable esterification catalyst/reagent. Another objective of the present invention is to avoid the use of cyclic lactide for the preparation of the alkyl lactyl lactate. Another objective of the present invention is to examine the transesterifcation—polycondensation of the ester to produce poly lactic acid.

OBJECTIVE OF THE INVENTION

One of the objectives of the present invention is to prepare a monomer containing two functional groups, namely, a hydroxyl and an ester group with adequate purity by a simple esterification reaction of hydroxyl acid with hydroxyl ester in the presence of suitable catalysts or reagents.

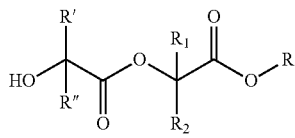

R=Me, Et, propyl
R'=H, Me, Et
R"=H, Me, Et
$R_1$=H, Me, Et
$R_2$=H, Me, Et

Typical Chemical Structure of Esters

Another objective of the present invention is to provide a process for the preparation of a novel linear monomer (1-methoxy-1-oxopropane-2-yl 2-hydroxypropionate) or methyl lactyllactate (MLL) of adequate purity.

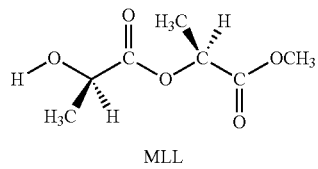

MLL

Chemical Structure of MLL

Yet another objective of the present invention is to provide a process for the preparation of poly-lactic acid (PLA) from methyl lactyl lactate (MLL) using a suitable catalyst.

SUMMARY OF THE INVENTION

Accordingly, the present invention provides a process for the preparation of an alkyl lactyl lactate by a simple esterification reaction of acid with alkyl lactate in presence of suitable catalysts or reagents comprising the steps of:
a) stiffing a mixture of alkyl lactate, condensing reagents in anhydrous solvent at 0° C.;
b) adding a solution of acid in a suitable chlorinated solvent to the reaction mixture of step (a) slowly over a period of 1-3 hours;
c) stiffing the reaction mixture at a temperature 27° C. for 10-12 hours to afford the product alkyl lactyl lactate.

The present invention further provides a process for the preparation of poly lactic acid from alkyl lactyl lactate using a suitable catalyst comprising the steps of:
a. subjecting alkyl lactyl lactate to polymerization at a temperature ranging from 130 to 160° C. for a period of 2 to 3 hours under nitrogen atmosphere followed by increasing temperature and decreasing the pressure in a step-wise manner i.e. 1.5 to 2 h at 100-110 mm, Hg at the same temperature, 30-40 mm, Hg for 1-1.5 h and finally at 1 to 1.5 h at 0.01 to 0.1 mm, Hg at 140 to 160° C. with continuous stiffing at 60-70 RPM to obtain a viscous oligomer;
b. charging the oligomer with a catalyst (0.05 to 1 wt %);
c. continuing the polymerization at 140 to 160° C. for 1 to 1.5 h under nitrogen atmosphere followed at 160 to 170° C. for 1 to 1.5 h at 100-110 mm, Hg, further followed at 160 to 170° C. for 1 to 1.5 h at 10 to 20 mm, Hg and finally carried out polymerization at 170° C. for 2 to 2.5 h at 0.01 to 0.1 mm, Hg to obtain a polymer of poly lactic acid.

DETAILED DESCRIPTION OF THE INVENTION

Figure 1:
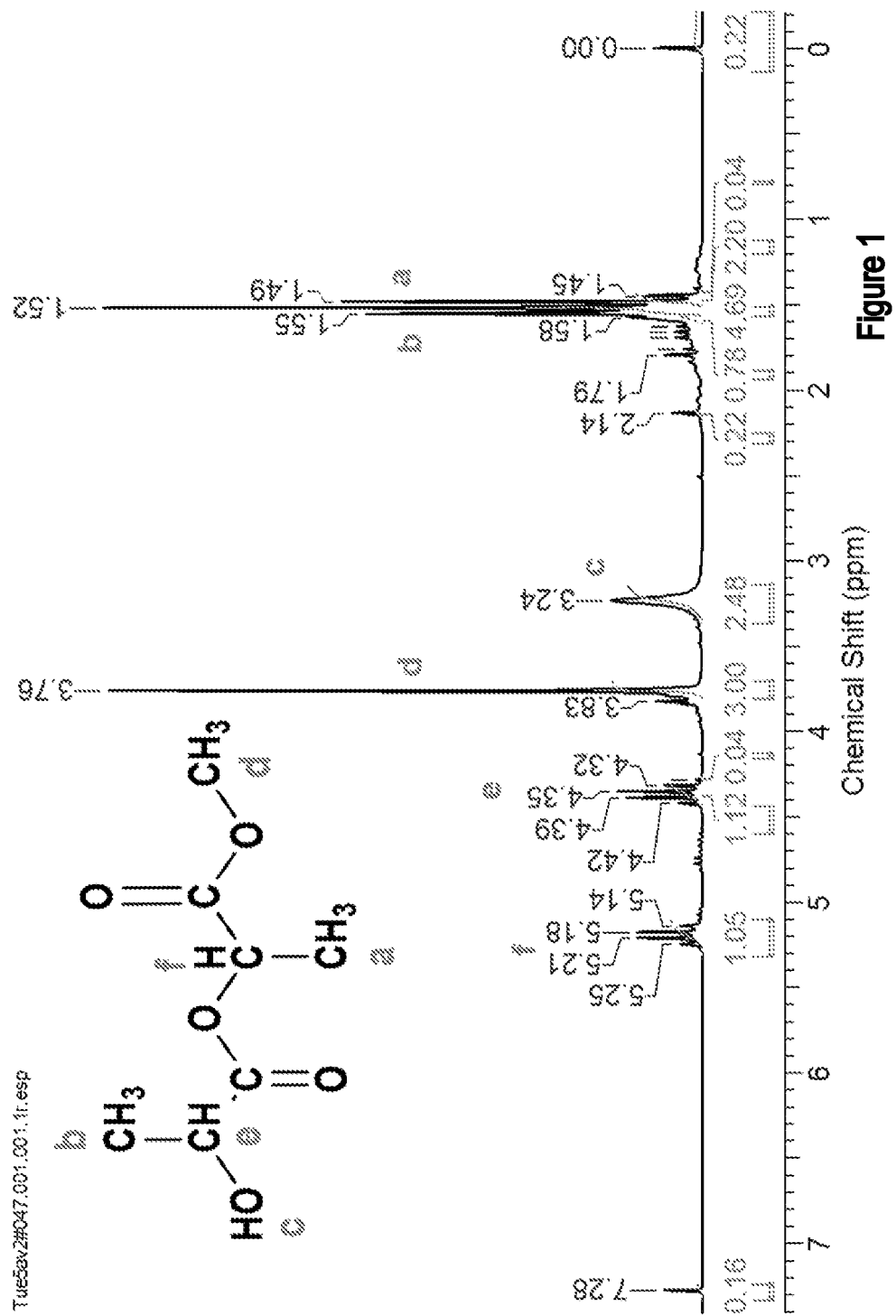
FIG. 1: $^1$H NMR (200 MHz) spectrum of MLL in $CDCl_3$.
Figure 2:
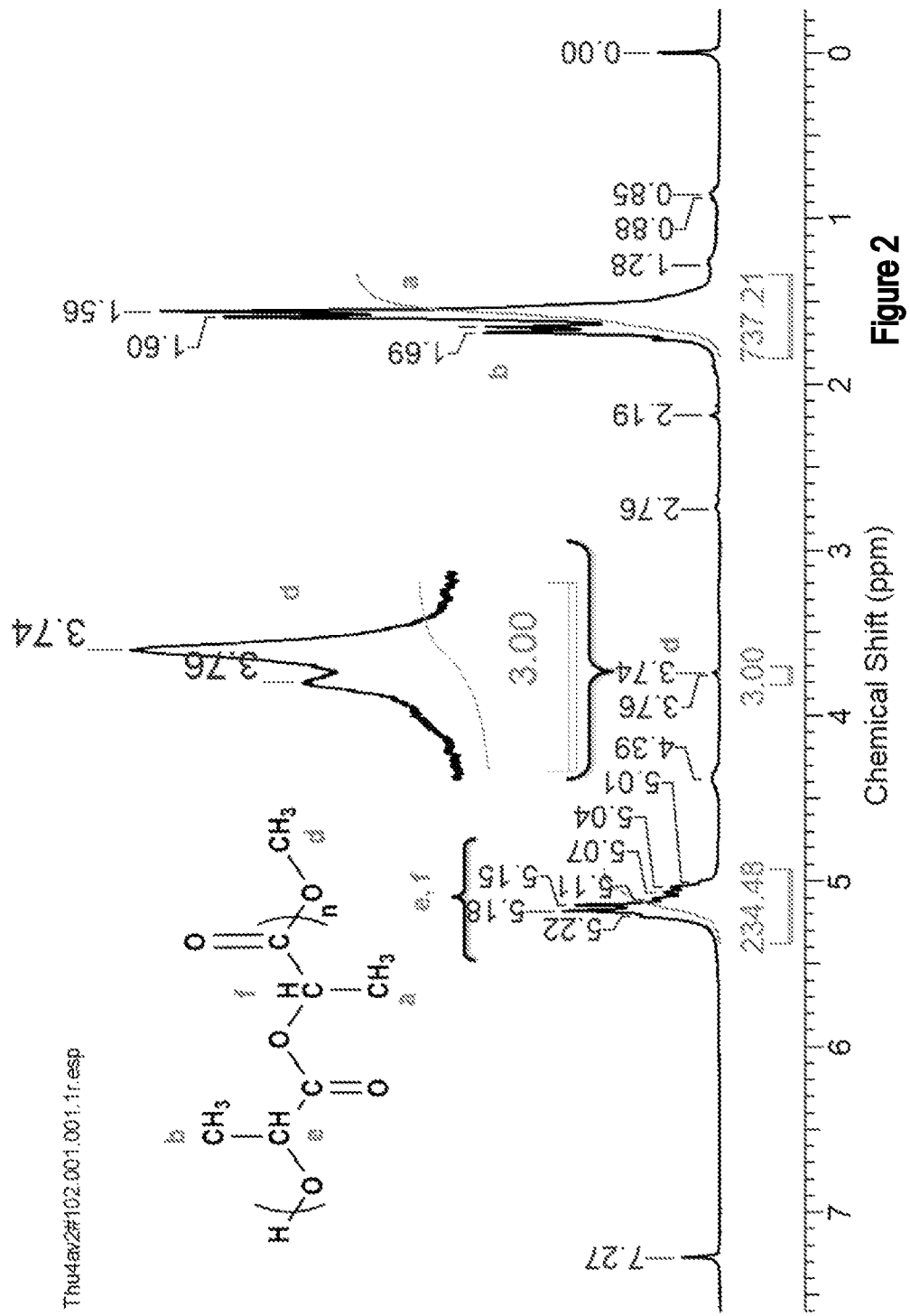
FIG. 2: $^1$H NMR (200 MHz) spectrum of PLA in $CDCl_3$.

The invention will now be described in detail in connection with preferred and optional embodiments so that various aspects thereof may be more fully understood and appreciated.

In view of above, the present invention provides a novel process for the preparation of hydroxyl functional esters.

More particularly the present invention provides a process for the preparation of an alkyl lactyl lactate by a simple esterification reaction of acid with alkyl lactate in presence of suitable catalysts or reagent comprising the steps of:
a) stirring the reaction mixture of alkyl lactate, condensing reagents in anhydrous solvent at 0° C.;
b) adding a solution of acid in solvent to a reaction mixture of step (a) slowly over a period of 1-3 hours;
c) stiffing the reaction mixture at temperature 27° C. for 10-12 hours to afford the product of monomer of alkyl lactyl lactate.

The purification of alkyl lactyl lactate is performed by filtering the solids from the solution of the ester in dichloromethane followed by evaporation of dichloromethane.

In an embodiment, said alkyl lactate can be either a methyl or ethyl ester.

In an embodiment, said alkyl lactate is methyl lactate.

In yet still another embodiment, said alkyl lactyl lactate is methyl or ethyl lactyl lactate.

In another embodiment, said reagents used for esterification are chosen from the broad family of carbodiimides comprising of dicyclohexylcarbodiimide, diisopropylcarbodiimide, 1,1-carbonylbiimidazole, 1-ethyl-3-(3-dimethylaminopropyl)carbodiimide, etc used along with an organic base such as pyridine, dimethylaminopyridine (DMAP) and the like.

In yet another embodiment, said 1.01 equivalent moles of carbodiimide and catalytic amount i.e., 10 mol percent of dimethylaminopyridine (DMAP) are used for the preparation of methyl lactyl lactate. In an embodiment, said acid is L(+)-lactic acid.

In yet another embodiment, said acid is lactic acid as a solution in a chlorinated solvent chosen from dichloromethane, chloroform, 1,2-dichloroethane, etc.

In yet still another embodiment the present invention provides a process for the preparation of poly lactic acid from alkyl lactyl lactate by using a suitable catalyst comprising the steps of:
a) subjecting alkyl lactyl lactate to melt polymerization at temperature ranging from 140 to 160° C. for a period of 2 to 3 h under nitrogen atmosphere followed by increasing temperature and decreasing the pressure in a step-wise manner i.e. 1.5 to 2 h at 100-110 mm, Hg at the same temperature, 30-40 mm, Hg for 1-1.5 h and finally at 1 to 1.5 h at 0.01 to 0.1 mm, Hg at 140 to 160° C. with continuous stiffing at 60-70 rpm to obtain a viscous oligomer;
b) charging the oligomer with a metal catalyst (0.05 to 1 wt %);
c) continuing the polymerization at 140 to 160° C. for 1 to 1.5 h under nitrogen atmosphere followed at 160 to 170° C. for 1 to 1.5 h at 100-110 mm, Hg, further followed at 160 to 170° C. for 1 to 1.5 h at 10 to 20 mm, Hg and finally carried out polymerization at 170° C. for 2 to 2.5 h at 0.01 to 0.1 mm, Hg to obtain a solid polymer of poly lactic acid.

In yet still another embodiment, said alkyl lactyl lactate is methyl lactyl lactate.

In yet still another embodiment, the said metal catalyst chosen from the family of transesterication and polycondensation catalysts, understood by those well versed in the art, such as, alkoxides of Group IV A metals (titanium alkoxides, zirconium alkoxides etc.), esters of Group IV B metals (e.g stannous octoate, di-n-buylyltin dilaurate, stannoxanes, etc), oxides of antimony (antimony trioxide) esters of bismuth (e.g bismuth triflate), alkoxides of aluminum (e.g aluminum isopropoxide), and esters of rare earth metals (e.g scandium triflate, ytterbium triflate, cerium triflate and the like).

In still another embodiment, said metal catalyst is selected from titanium or tin.

In yet still another embodiment, said metal catalyst is selected from 0.05 to 1 weight percent of titanium or tin.

In yet still another embodiment, said poly acid is poly (lactic acid).

The following examples, which include preferred embodiments, will serve to illustrate the practice of this invention, it being understood that the particulars shown are by way of example and for purpose of illustrative discussion of preferred embodiments of the invention.

Example 1: Preparation of Methyl Lactyl Lactate

To a 500 mL three necked glass reactor equipped with mechanical stirrer and reflux condenser was added methyl lactate (29.54 g, 0.284 mol) in anhydrous $CH_2Cl_2$, 4-dimethylamino pyridine (3.47 g, 0.0284 mol) and dicyclohexylcrbodiimide (64.66 g, 0.313 mol) in anhydrous $CH_2Cl_2$ (50 mL) at 0° C. and the mixture was stirred. Lactic Acid (28.10 g, 258 mL, 1.21 N in $CH_2Cl_2$, 0.312 mol) was added dropwise over a period of 2 hours and the reaction continued at room temperature for 24 hours. The precipitated dicyclohexyl urea obtained was separated by filtration. The solvent was evaporated and the residue dissolved in diethyl ether, filtered followed by addition of 10% acetic acid solution. The organic layer was washed three times with aqueous sodium bicarbonate solution and water, dried over sodium sulphate, filtered and the solvent evaporated to give the desired product, 29 g (58% yield).

Example 2: Polymerization of Methyl Lactyl Lactate using Stannous Chloride/PTSA Catalyst To a three neck glass reactor equipped with mechanical stirrer, nitrogen gas inlet and vacuum was added 1.4 g of MLL and the oligomerization started at 140° C. for 3 h under inert atmosphere, temperature was increased to 160° C. for 3 h and the reaction mixture was cooled to room temperature. Stannous chloride/PTSA (0.05 wt. %) catalyst was added and polymerization was continued in a stepwise manner: 140° C. at 0.05 mm of Hg for 2 h, 160° C. at 0.05 mm of Hg for 2 h and 170° C. at 0.05 mm of Hg for another 3 h respectively. The viscous solid material obtained was cooled to room temperature, dissolved in chloroform and precipitated in pet ether, dried under reduced pressure and characterized by different techniques. The number average molecular weight of the poly(lactic acid) was found to be 17000 g/mol.

Example 3: Polymerization of Methyl Lactyl Lactate using Titanium Isopropoxide

To a three neck glass reactor equipped with mechanical stirrer, nitrogen gas inlet and vacuum was added 1.4 g of MLL and the oligomerization started at 140° C. for 3 h under inert atmosphere, temperature was increased to 160° C. for 3 h and the reaction mixture was cooled to room temperature. Titanium isopropoxide (0.05 wt. %) catalyst was added and the polymerization was continued in a stepwise manner: 140° C. at 0.05 mm Hg for 2 h, 160° C. at 0.05 mm Hg for 2 h, and 180° C. at 0.05 mm Hg for 3 h respectively. The cool viscous solid material obtained was cooled to room temperature, dissolved in chloroform and precipitated in pet ether, dried under reduced pressure and characterized by different techniques. The number average molecular weight of the poly(lactic acid) was found to be 17000 g/mol.

Example 4: Polymerization of Methyl Lactyl Lactate using Titanium Isopropoxide

In a 15 mL three neck round bottom flask equipped with magnetic stirrer, $N_2$ inlet and ice cold coiled trap via air condenser was charged with methyl lactyl lactate (2 g) and titanium isopropoxide (0.033 g, 0.5 wt %) under nitrogen. The flask was immersed in oil bath, temperature reached 140° C. after 30 minutes. Methanol formation was observed at the top of flask. The reaction was continued till methanol formation ceased. The reaction was continued for another 30 min. A polymer of number average molecular weight of 1200 g/mol was obtained in 99% yield.

Advantages of the Invention

A method of preparation of an alkyl lactyl lactate;

A method of preparation of alkyl lactyl lactate which does not involve the use of a cyclic dimer of Lactic acid, namely, lactide;

An alkyl lactyl lactate monomer which is a liquid having high boiling point and can be obtained in anhydrous condition;

A method for polymerizing the alkyl lactyl lactate by transesterication-polycondensation process to produce poly lactic acids in good yields and substantially free of cyclic oligomers as impurity.

We claim:
1. A novel process for the preparation of a alkyl lactyl lactate comprising the following steps:
   a) stirring the reaction mixture of alkyl lactate, condensing reagents in anhydrous solvent at 0° C.;
   b) adding a solution of acid in solvent to a reaction mixture of step (a) slowly over a period of 1 to 3 hours;
   c) stirring the reaction mixture at temperature 27° C. for 10 to 12 hours to afford the product of monomer of alkyl lactyl lactate.
2. The process as claimed in claim 1, wherein said alkyl lactate is methyl lactate.
3. The process as claimed in claim 1, wherein said alkyl lactyl lactate is methyl lactyl lactate.
4. The process as claimed in claim 1, wherein said condensing reagents are dicyclocarbodiimide and dimethylamino pyridine.
5. The process as claimed in claim 1, wherein said acid is L(+)-lactic acid.
6. The process as claimed in claim 1, wherein said solvent is dichloromethane.

* * * * *